United States Patent [19]
Daoudal

[11] Patent Number: 5,725,879
[45] Date of Patent: Mar. 10, 1998

[54] VETERINARY TABLET INTENDED ESPECIALLY FOR CATS

[76] Inventor: José Daoudal, 10, Avenue General Patton, 53031 Laval, France

[21] Appl. No.: 300,152

[22] Filed: Sep. 1, 1994

[30] Foreign Application Priority Data

Sep. 1, 1993 [FR] France .................. 93 10422

[51] Int. Cl.$^6$ ............................... A61K 9/20
[52] U.S. Cl. ............... 424/464; 424/441; 424/442; 424/439; 424/467
[58] Field of Search ............... 424/442, 464, 424/438, 439, 441, 467

[56] References Cited

U.S. PATENT DOCUMENTS

| | | | |
|---|---|---|---|
| D. 228,456 | 9/1973 | Ninger | D16/3 |
| 2,052,376 | 8/1936 | Zellers | 167/53 |
| 4,735,805 | 4/1988 | Ni et al. | 424/464 |
| 4,824,677 | 4/1989 | Shah et al. | 424/467 |
| 4,857,333 | 8/1989 | Harold | 424/442 |

FOREIGN PATENT DOCUMENTS

| | | |
|---|---|---|
| 0 396 335 A1 | 11/1990 | European Pat. Off. . |
| 0 531 964 A1 | 3/1993 | European Pat. Off. . |
| 2 057 878 | 4/1981 | United Kingdom . |

*Primary Examiner*—Thurman K. Page
*Assistant Examiner*—James M. Spear
*Attorney, Agent, or Firm*—Wolf, Greenfield & Sacks, P.C.

[57] ABSTRACT

A veterinary tablet promotes the ingestion of medicinal substances by domestic animals, especially by cats. The tablet possesses an oblong shape completely lacking rotational symmetry.

15 Claims, 1 Drawing Sheet

VETERINARY TABLET INTENDED ESPECIALLY FOR CATS

The present invention relates to a veterinary tablet enabling the taking of medicinal substances by domestic animals, especially by cats, to be facilitated.

The number of domestic animals such as dogs and cats is ever increasing. Concomitantly with this increase, changes are being witnessed in the treatments given to these animals.

It is an undeniable fact that, at the present time, the treatments administered are not always properly complied with on account of the difficulty of making the animal take medication.

It was realized, according to the invention, that, in cats, one of the reasons for this difficulty is linked with the round shape of conventional tablets; in effect, the animal to which such tablets are offered tends to make them roll, triggering in it a play reflex, the consequence of which is that the administration is refused.

The outcome of this observation is that it was ascertained that, surprisingly, the shape of the tablets influences to a large extent their ability to appeal to cats.

The objective of the invention is to use this finding in order to propose a veterinary tablet, intended more especially for cats, which is capable of being taken spontaneously by the animal.

According to the invention, such a tablet is characterized in that it possesses an oblong shape completely lacking rotational symmetry.

According to a preferential feature of the invention, this tablet possesses two identical, essentially oval principal faces separated by a lateral cylindrical surface whose generatrix is essentially perpendicular to the principal faces.

It was possible to ascertain that such a tablet the principal faces of which are often slightly domed outwards for reasons of ease of manufacture is readily accepted by the animal as a result of its non-rotatory character, but also owing to the fact that it is easier to grasp, this also being likely to enhance the appetency.

It was possible to establish, according to another especially advantageous feature of the invention, that the latter may be further improved by providing for a narrowing in the middle part of the tablet.

The presence of such narrowing proves, in effect, likely to make it easier, to a large extent, for the cat to grasp the tablet.

It is, moreover, customary to put on sale, both in the medical field and in the veterinary field, divisible tablets which make it possible to comply more particularly with the dosage regimen per kg body weight of the patient or animal to be treated; it is, in effect, often necessary to distribute only halves of tablets in order to suit the dosage.

Now, it was realized, according to another feature of the invention, that the fact of equipping one of the principal faces of the tablet in its middle part with a groove serving as a breakline in no way detracts from the ease of grasp of the tablet by the cat.

It is hence especially advantageous to provide for such breaklines.

The dimensions of the above-mentioned veterinary tablet, although they do not impose a limitation on the invention, must naturally be suited to the average size of the cats for which the tablets are more particularly intended.

For this reason, the principal faces of the tablet are, on average, of the order of from about 6 to about 15 mm in length for a maximum width of the order of from about 4 to about 6 mm; the width in the region of the narrowing is, for its part, usually of the order of from about 3.5 to about 5.5 mm, meaning that there is on average a difference of approximately 0.5 mm between the maximum width and the minimum width in the region of the narrowing.

Tests performed using tablets 11 mm in length, 5 mm in maximum width and 4.5 mm in width in the region of the narrowing enabled satisfactory appetency features to be demonstrated in virtually all cats.

The thickness of the tablet can vary to a relatively large extent in accordance with the nature of the preventive or curative treatment for which it is intended and the type of active principle which it has to contain; it is nevertheless usual to opt for dimensions enabling an average weight of the order of from about 120 to about 200 mg to be obtained for each tablet.

Naturally, the veterinary tablet according to the invention can contain various types of orally administrable active principles, or medicinal substances chosen from all existing and future therapeutic and dietary classes, among which the following examples may be mentioned: Examples of therapeutic classes:

Anti-infectious agents (antibiotics, sulphonamides, etc.),

Agents for treating internal parasites,

Anti-inflammatories and antihistaminics,

Oral vaccines,

Hormones,

Substances for digestive therapy, such as gastrointestinal dressings and sedatives, replacement floras, antidiarrhoeals, hepatoprotective agents, antispasmodics, laxatives, intestinal antiseptics, oral rehydrating agents, etc., Substances for cardiovascular therapy, such as cardiac and cardiovascular analeptics, haemostatic agents, vasoconstrictors and -dilators, etc., Substances for respiratory therapy, such as respiratory analeptics, antitussives, bronchodilators, bronchosecretolytics, respiratory antiseptics, Substances which act on the nervous system: analgesics, sedatives and tranquillizers, antiepileptics, anaesthetics, appetite stimulants and anorectics, etc., Immunotherapeutics substances, such as immunosuppressants, immunostimulants, replacement immunoglobulins, etc.

Diuretics,

Anticancer substances such as antimitotics,

Macro- and trace elements,

Vitamins,

Amino acids and proteins,

Fatty acids,

Carbohydrates,

Extracts of plants or of animal organs.

Independently of the foregoing, many substances for the treatment or prevention of diseases and organic imbalances are known to exert an effect which is repellant to cats' sense of smell, the latter animals refusing to take them. To remedy this drawback, and in a manner known per se, it is possible to make provision, according to the invention, for combining the active principle or principles present in the tablet with an appealing matrix such as, for example, a mixture of liver powder and brewer's yeast, which has proved especially well-liked by cats, or alternatively a mixture of different animal and/or vegetable proteinaceous substances; it has been possible, in particular, to establish that the use of fishmeal can increase the appetency of some active principles.

The active principles may be simply incorporated in such a matrix or made into a core which is itself included therein in a manner known, in particular, from the document EP-0, 320,320 B1, incorporated herein by reference.

As a non-limiting example, the tablet according to the invention can advantageously possess, as active principle, amoxycillin, in particular in trihydrate form, at a dose of 40 mg per 175 mg of tablet.

The features of the veterinary tablet which forms the with reference to the attached drawing, which is diagrammatic subject of the invention will be described in greater detail representation of such a tablet on a very greatly enlarged scale.

BRIEF DESCRIPTION OF THE DRAWING

According to the FIGURE, the tablet, of oblong general shape, possesses two identical principal faces 1, only one of which is visible, which are separated by a lateral cylindrical surface 2 whose generatrix (x–x') is essentially perpendicular to the principal faces 1. The latter, of essentially oval shape, are slightly domed outwards, and possess in their middle part a narrowing 3 which makes it easier for the cats to grasp the tablet.

The dimensions of this tablet, suited to the morphology of cats, can advantageously be as follows:

Figure 1:
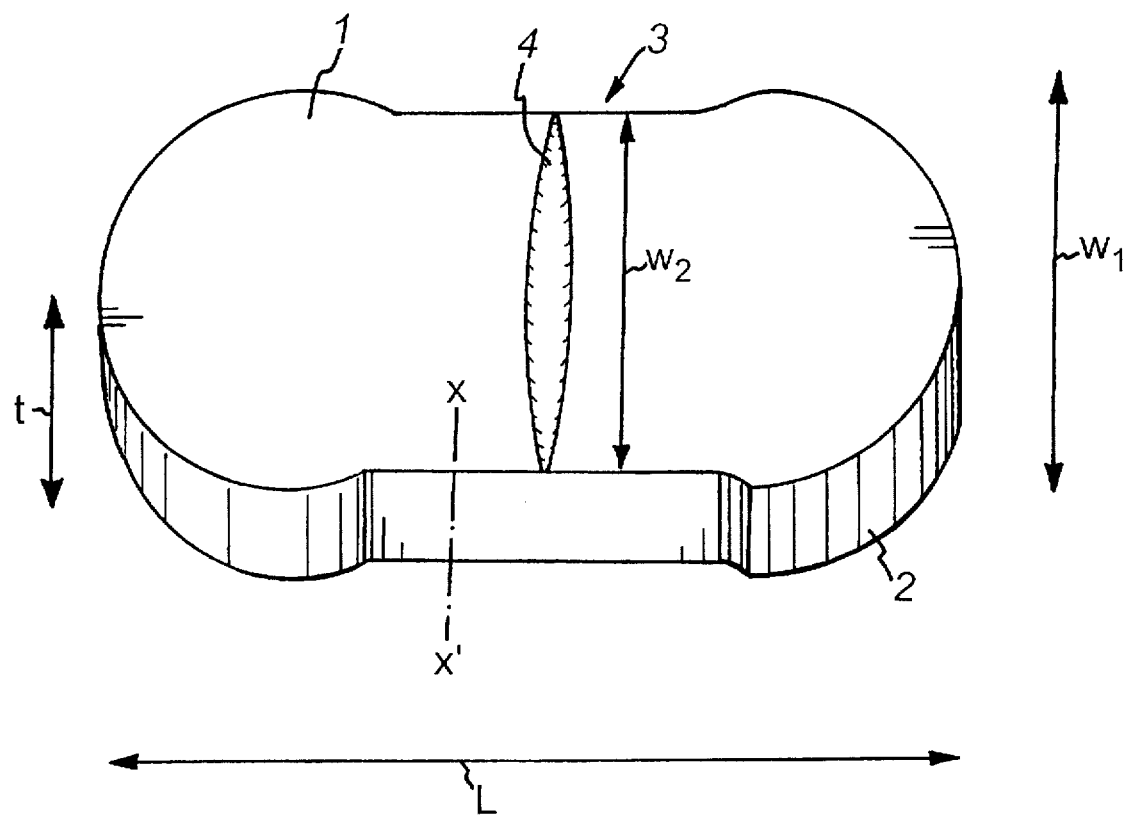

length L: 11.0 mm maximum width $w_1$: 5.0 mm width in the region of the narrowing 3: 4.5 mm These dimensions are naturally not to be considered to impose a limitation on the invention.

The thickness t of this tablet can, for its part, vary significantly in accordance with the type of treatment for which it is intended.

According to the FIGURE, the tablet possesses, in the middle part of one of the principal faces 1, a groove 4 serving as a breakline.

It was possible to ascertain that the fact of dividing the tablet into two halves in no way detracts from the ease of grasp for the cat.

I claim:

1. A method of administering to an animal a medicinal substance comprising the step of:

presenting to an animal a veterinary tablet constructed and arranged to resist rolling on a surface and said tablet containing a medicinal substance incorporated throughout a matrix.

2. The method as recited in claim 1, wherein the veterinary compound has an oblong shape and lacks rotational symmetry.

3. The method as recited in claim 1, wherein the veterinary compound possesses two identical, essentially oval principal faces separated by a lateral cylindrical surface whose generatrix is essentially perpendicular to the principal faces.

4. The method as recited in claim 3, wherein the principal faces are slightly domed outwards.

5. The method as recited in claim 3, wherein the oval faces have an essentially hour-glass shape such that the veterinary compound has end regions separated by a central region that is narrow relative to the end regions.

6. A method of administering to a cat a medicinal substance comprising:

presenting to a cat a tablet containing a medicinal substance, wherein the tablet has an oblong shape lacking rotational symmetry, the shape selected to prevent rolling of the tablet on a surface and said tablet containing a medicinal substance incorporated throughout a matrix.

7. A method of administering to an animal a medicinal substance comprising the step of:

presenting to an animal a veterinary compound containing a medicinal substance, the compound being constructed and arranged into a shape which resists rolling on a surface, and possessing two identical, essentially oval principal faces separated by a lateral cylindrical surface whose generatrix is essentially perpendicular to the principal face, and wherein at least one of the principal faces includes a central region including a groove serving as a breakline.

8. A method of administering to an animal a medicinal substance comprising:

presenting to an animal a veterinary compound containing a medicinal substance, constructed and arranged to resist rolling on a surface, wherein the veterinary compound possesses two identical, essentially oval principal faces separated by a lateral cylindrical surface whose generatrix is essentially perpendicular to the principal faces, and wherein the principal faces each have a length of from about 6 mm to about 15 mm, and each have a maximum width of from about 4 mm to about 6 mm.

9. A method of administering to an animal a medicinal substance comprising:

presenting to an animal a veterinary compound, containing a medicinal substance, constructed and arranged to resist rolling on a surface, wherein the veterinary compound possesses two identical, essentially oval principal faces separated by a lateral cylindrical surface whose generatrix is essentially perpendicular to the principal faces, wherein the oval faces have an essentially hour-glass shape such that the veterinary compound has end regions separated by a central region that is narrow relative to the end regions, and wherein the principal these each have a width, in the central region, of from about 3.5 mm to about 5.5 mm.

10. The method as recited in claim 1, wherein the veterinary compound includes a substance that appeals to the animal.

11. The method as recited in claim 10, wherein the substance that appeals to the animal comprises a mixture of liver powder and brewer's yeast.

12. The method as recited in claim 10, wherein the substance that appeals to the animal comprises a mixture of proteinaceous substances of animal and/or vegetable origin.

13. The method as recited in claim 1, wherein the medicinal substance comprises amoxycillin, in trihydrate form.

14. The method as recited in claim 1, wherein the animal is a cat.

15. A method of administering to an animal a medicinal substance comprising:

presenting to an animal a veterinary compound, containing a medicinal substance, constructed and arranged to resist rolling on a surface, wherein the veterinary compound has an average weight of from about 120 mg to about 200 mm.

\* \* \* \* \*